United States Patent [19]

Fukazawa et al.

[11] Patent Number: 5,463,061

[45] Date of Patent: Oct. 31, 1995

[54] PROCESS FOR PRODUCTION OF GLYCIDE DERIVATIVE

[75] Inventors: Nobuyuki Fukazawa; Tsuneji Suzuki; Nobuya Kawauchi; Hironori Komatsu; Kengo Otsuka; Yuki Nakajima, all of Mobara, Japan

[73] Assignee: Mitsui Toatsu Chemicals, Incorporated, Tokyo, Japan

[21] Appl. No.: 175,397

[22] PCT Filed: May 13, 1993

[86] PCT No.: PCT/JP93/00626

§ 371 Date: Jan. 13, 1994

§ 102(e) Date: Jan. 13, 1994

[87] PCT Pub. No.: WO93/23386

PCT Pub. Date: Nov. 25, 1993

[30] Foreign Application Priority Data

May 15, 1992 [JP] Japan .................................. 4-123338

[51] Int. Cl.$^6$ ................................................ C07D 215/20
[52] U.S. Cl. .......................... 546/158; 546/141; 546/290; 548/484; 548/136; 549/466; 549/475; 549/462
[58] Field of Search ........................ 546/158, 141, 546/290; 514/312; 548/136, 484; 549/462, 466, 475

[56] References Cited

U.S. PATENT DOCUMENTS 5,082,847  1/1992  Pascal ................................ 514/312

OTHER PUBLICATIONS

Klunder, "Arenesulfonate Derivatives of Homochiral Glycidol: Versatile Chiral Building Blocks for Organic Synthesis", *J. Org. Chem.*, vol. 54 pp. 1295–1304, 1989.

*Hackh's Chemical Dictionary*, 3rd Edition, edited by Julian Grant, p. 31, 1944.

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

A glycide derivative represented by the following general formula (I) is produced by reacting a hydroxyaryl or heteroaryl represented by A-OH with glycidyl tosylate in the presence of a cesium base as a base. Thereby, an aryl glycidyl ether derivative, which is an important intermediate for drug production, can be produced easily and reliably. Particularly when optically active glycidyl tosylate is used, said compound can be obtained at a high optical purity.

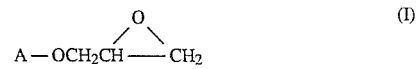

wherein A represents an aryl group or a heteroaryl group.

15 Claims, No Drawings

PROCESS FOR PRODUCTION OF GLYCIDE DERIVATIVE

DESCRIPTION

This application is the national phase of PCT/JP93/00626, filed May 13, 1993.

TECHNICAL FIELD

The present invention relates to a process for producing a glycide derivative (an aryl glycidyl ether or heteroaryl glycidyl ether derivative) which is an important intermediate in production of drugs, particularly circulatory drugs, carcinostaticity-enhancing agents, etc. More particularly, the present invention relates to a process for producing a glycide derivative at a high efficiency and economically and, when the product is an optically active substance, at a high optical purity.

BACKGROUND ART

Glycide derivatives are important intermediates in production of various drugs. So-called β-blockers, which are in wide use as, for example, circulatory drugs, particularly an antiarrhythmic drug and an antihypertensive drug, are produced basically using a glycide derivative as an important intermediate. The process for production of propranolol hydrochloride as an typical example of β-blockers is shown below. Other β-blockers are produced by similar reactions wherein other hydroxyaryl is used as a starting material in place of α-naphthol and a glycide derivative is used as an intermediate.

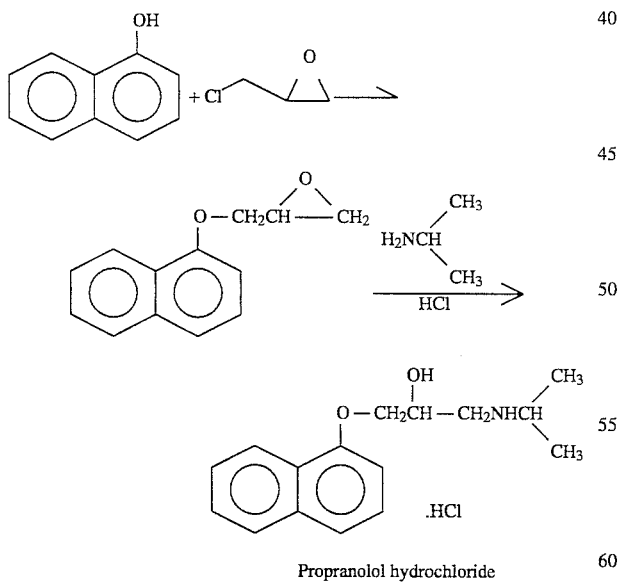

Propranolol hydrochloride

Quinoline derivatives used as a carcinostaticity-enhancing agent, etc., disclosed in Japanese Patent Application Kokai (Laid-Open) No. 101662/1991, etc. are produced by the following process using a glycide derivative as an intermediate.

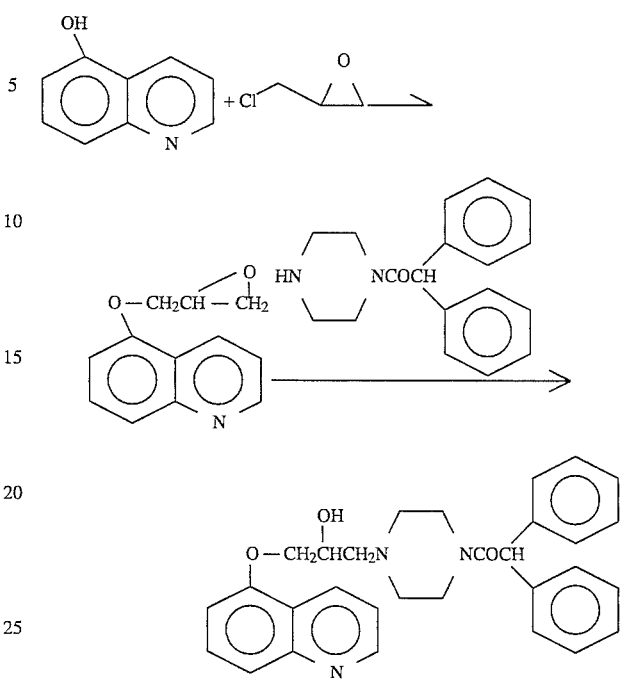

As appreciated from these cases, glycides are important compounds in drug production. For production of glycides, there have conventionally been known, as shown previously, processes of reacting a corresponding hydroxyaryl with epichlorohydrin or glycidyl tosylate in the presence of a base of a metal such as sodium, potassium or the like or an organic base such as triethylamine, pyridine or the like. These processes, however, have had many problems in operation, safety, etc. in industrial large amount production and also problems in efficiency and economy.

Meanwhile, a series of these drugs each have an asymmetric carbon and are each an optically active substance. In recent years, in the development of drugs using optically active substances, the physiologically activities of each optically active substance have been investigated. In some cases, the optically active substance itself is used as a drug as in the case of, for example, penbutolol sulfate shown below.

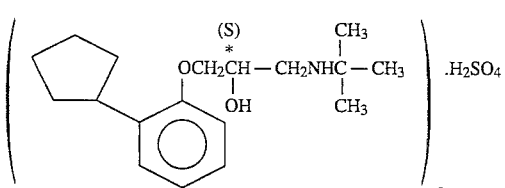

Penbutolol sulfate
(*C refers to an asymmetric carbon, and S refers to a S-confiugation.)

Hence, it is an important task to establish processes for producing a series of the above products each in the form of an optically active substance easily and at a high optical purity (enantiomer excess % [% e.e.]). In order to achieve the task, it has hitherto been investigated to use optically active epichlorohydrin or optically active glycidyl tosylate in combination with various bases. Examples of such approaches are reported in Japanese Patent Application Kokai (Laid-Open) No. 121282/1989, Japanese Patent Application Kokai (Laid-Open) No. 279890/1989, Japanese Patent Application Kokai (Laid-Open) No. 279887/1989, European Patent 454385, Chem. Pharm. Bull., 35, 8691 (1987), Chem. Pharm. Bull., 38, 2092 (1990), J. Org. Chem., 54, 1295 (1989), etc. Of these processes, however, for example, when there are used sodium hydride as a metal base and dimethylformamide as a solvent and there are reacted 5-hydroxyquinoline and glycidyl tosylate, the resulting glycidyl ether has an optical purity of 80% e.e. or below, which is not satisfactory. That is, the above-mentioned optically active compounds have two reaction sites as shown below; their reactions are difficult to control; no process capable of producing an intended product at a satisfactory optical purity has been established yet.

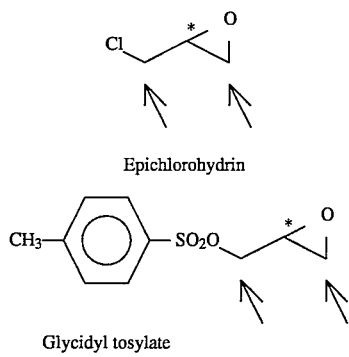

Epichlorohydrin

Glycidyl tosylate

Thus, there has been desired a novel process for producing a glycide derivative which is an important intermediate in drug production, efficiently and economically. There has also been strongly desired a process for producing said glycide derivative in the form of an optically active substance, easily and at a high optical purity.

DISCLOSURE OF THE INVENTION

The present inventors made an extensive study in order to solve the above problems. As a result, the present inventors found that a glycide derivative can be produced efficiently and economically by reacting a hydroxyaryl or heteroaryl derivative with glycidyl tosylate in the presence of a cesium base as a base. The present inventors further found that when optically active glycidyl tosylate is used as the glycidyl tosylate, the cesium salt can surprisingly bring about the formation of an optically active substance at a very high yield. The findings have led to the completion of the present invention. The glycide derivative includes an aryl glycidyl ether derivative and a heteroaryl glycidyl ether derivative.

The present invention resides in a process for producing a glycide derivative represented by the following general formula (I), which is characterized by reacting a hydroxyaryl or heteroaryl represented by A-OH, with glycidyl tosylate in the presence of a cesium base as a base:

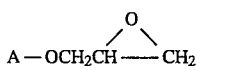

wherein A represents an aryl group or a heteroaryl group.

The present invention resides also in a process according to the above, wherein an optically active glycidyl derivative represented by general formula (I) is produced using optically active glycidyl tosylate as the glycidyl tosylate.

BEST MODE FOR CARRYING OUT THE INVENTION

Herein, the cesium salt refers to a cesium base such as cesium hydroxide, cesium carbonate or the like; the aryl group refers to a carbon aromatic ring such as phenyl group, naphthyl group, indenyl group or the like; and the heteroaryl group refers to a heterocyclic aromatic ring such as indolyl group, furyl group, thienyl group, pyridyl group, quinolyl group, isoquinolyl group, benzofuryl group, thiadiazolyl group or the like. The aryl group or the heteroaryl group includes those having a substituent such as alkyl group, cycloalkyl group, hydroxy group, alkoxy group, halogen atom, acyl group, cyano group or the like.

Also, the glycidyl tosylate includes glycidyl benzenesulfonate, glycidyl nitrobenzenesulfonate, etc. In reacting them, a water solvent, an organic solvent or a mixed solvent thereof is used. As the organic solvent, there are used alcohol solvents such as methanol, ethanol and the like; ether solvents such as ethyl ether, tetrahydrofuran and the like; amide solvents such as dimethylformamide, dimethylimidazolidinone and the like; hydrocarbon solvents such as hexane, benzene, toluene and the like; acetonitrile; dimethyl sulfoxide; and so forth. The temperature can range from 0° C. to the boiling point of the solvent used, but is preferably in the range of room temperature to 70° C.

The amount of the cesium salt used has no particular restriction, but is ordinarily 0.1–10 equivalents, preferably about 1–3 equivalents per mole of A-OH (hydroxyaryl or heteroaryl).

The amount ratio of the hydroxyaryl or heteroaryl and the glycidyl tosylate is preferably an equimolar ratio. However, the reaction proceeds with no problem even though one of them is in excess, for example, 10 moles per mole of the other. An optically active glycide derivative can be obtained by using optically active glycidyl tosylate and the same reaction conditions as mentioned above. Particularly when cesium carbonate is used as the base and dimethylformamide is used as the solvent, it is possible to obtain an optical purity of at least about 90% e.e. (enantiomer excess).

EXAMPLES

The present invention is hereinafter described in more detail by way of Examples. However, the present invention is in no way restricted thereto.

Example 1

297 g of cesium carbonate was added to 600 ml of dimethylformamide. Further, 83.5 g of 5-hydroxyquinoline was added. The mixture was stirred at 25°–30° C. for 30 minutes. To the reaction mixture was slowly added 109 g of glycidyl tosylate. The resulting mixture was stirred at 25°–30° C. for 15 hours. The reaction mixture was poured into 3 liters of ice water, followed by stirring and extraction with 2 liters of ethyl acetate. The aqueous layer was subjected to extraction with 2 liters of ethyl acetate. The organic layers were combined and washed twice with 2 liters of water. The ethyl acetate layer was dried over anhydrous Glauber's salt and subjected to vacuum distillation to remove the solvent. The residue was purified by silica gel column chromatography (hexane:ethyl acetate=1:1) to obtain 76.8 g (yield: 66%) of intended 5-(2,3-epoxypropoxy)quinoline as a light yellow powder.

IR v (KBr) cm$^{-1}$: 3054, 1590, 1270, 1098, 915, 856, 797

NMR δ ppm (CDCl$_3$): 2.86 (m, 1H), 2.99 (m, 1H), 3.45–3.53 (m, 1H), 4.12 (dd,1H), 4.46 (m,1H), 6.89 (d, 1H), 7.43 (dd,1H), 7.62 (t,1H), 7.76 (d,1H), 8.67 (d,1H), 8.92 (dd,1H)

Example 2

255 mg of cesium carbonate was added to 3.7 ml of an ethanol solution containing 108 mg of 5-hydroxyquinoline, at room temperature. The mixture was stirred at room temperature for 3 hours, concentrated and dried at 5° C. under reduced pressure until the residue was solidified. The resulting solid was suspended in 3.2 ml of dimethylformamide. To the suspension was added 187 mg of R(–)-glycidyl tosylate (96% e.e.) at room temperature, followed by stirring for 12 hours to carry out a reaction. After the completion of the reaction, the reaction mixture was concentrated and mixed with water. The aqueous layer was subjected to extraction with 50 ml of ethyl acetate. The extract was washed with a saturated aqueous sodium chloride solution and dried over anhydrous magnesium sulfate, followed by concentration. The residue was purified by silica gel column chromatography (chloroform:methanol=100:1) to obtain 114 mg (yield: 76%) of intended R(–)-5-(2,3 -epoxypropoxy)quinoline (optical purity: 94% e.e.) as colorless powdery crystals. Its IR and NMR values were the same as those obtained in Example 1.

[α]D (23° C., EtOH, c=2.18)= –35.6°

Example 3

417 mg of cesium carbonate was added to 3.3 ml of ethanol. Further, 109 mg of phenol was added. The mixture was stirred at 25°–30° C. for 30 minutes. The reaction mixture was concentrated to dryness. Thereto were added 3.3 ml of dimethylformamide and 292 mg of R(–)-glycidyl tosylate (98.4% e.e.). The resulting mixture was stirred at 25°–30° C. for 15 hours. The reaction mixture was concentrated. The residue was purified by silica gel column chromatography (hexane:isopropanol= 50:1) to obtain 155 mg (yield: 89%) of intended R(–)-2,3-epoxypropoxybenzene (optical purity: 92% e.e.) as a colorless oily substance.

NMR δ ppm (CDCl$_3$): 2.76 (m,1H), 2.90 (m, 1H), 3.30–3.45 (m, 1H), 3.96 (dd,1H), 4.21 (m, 1H), 6.85–7.09 (m,3H), 7.21–7.41 (m,2H)

[α]D (24° C., MeOH, c= 2.86)= –14.1°

Example 4

365 mg of cesium carbonate was added to 8.8 ml of dimethylformamide. Further, 147 mg of 1-naphthol was added. The mixture was subjected to vacuum distillation to remove the solvent by half. To the resulting reaction mixture was added 256 mg of R(–)-glycidyl tosylate (98.4% e.e.). The resulting mixture was stirred at 25°–30° C. for 15 hours. The reaction mixture was concentrated. The residue was purified by silica gel column chromatography (hexane:isopropanol=50:1) to obtain 198 mg (yield: 97%) of intended R(–)-1-(2,3-epoxypropoxy)naphthalene (optical purity: 93% e.e.) as a colorless oily substance.

NMR δ ppm (CDCl$_3$): 2.85 (m, 1H), 2.96 (m, 1H), 3.43–3.51 (m, 1H), 4.14 (dd,1H), 4.40 (m,1H), 6,80 (d,1H), 7.32–7.52 (m,4H), 7.74–7.83 (m,1H), 8.24–8.34 (m,2H)

[α]D (24° C., MeOH, c= 3.85)= –36.6°

Example 5

363 mg of cesium carbonate was added to 9.8 ml of dimethylformamide. Further, 167 mg of 2-cyclopentylphenol was added. The mixture was subjected to vacuum distillation to remove the solvent by half. To the reaction mixture was added 254 mg of R(–)-glycidyl tosylate (98.4% e.e.). The mixture was stirred at 25°–30° C. for 15 hours. The reaction mixture was concentrated. The residue was purified by silica gel column chromatography (hexane:isopropanol= 50:1) to obtain 194 mg (yield: 86%) of intended R(–)-1-(2,3-epoxypropoxy)-2-cyclopentylbenzene (optical purity: 89% e.e.) as a colorless oily substance.

NMR δ ppm (CDCl$_3$): 1.46–2.12 (m,9H), 2.77 (m,1H), 2.91 (m,1H), 3.30–3.42 (m, 1H), 3.98 (dd,1H), 4.23 (m, 1H), 6.76–6.95 (m,2H), 7.08–7.28 (m, 1H)

[α]D (24° C., MeOH, c= 3.49)= –15.6°

Example 6

350 mg of cesium carbonate was added to 7.8 ml of dimethylformamide. Further, 130 mg of 4-hydroxyindole was added. The mixture was subjected to vacuum distillation to remove the solvent by half. To the resulting reaction mixture was added 245 mg of R(–)-glycidyl tosylate (98.4% e.e.). The mixture was stirred at 25°–30° C. for 15 hours. The reaction mixture was concentrated. The residue was purified by silica gel column chromatography (hexane:isopropanol=20:1) to obtain 134 mg (yield: 72%) of intended R(–)-4-(2,3-epoxypropoxy)indole (optical purity: 90% e.e.) as a colorless oily substance.

NMR δ ppm (CDCl$_3$): 2.82 (m, 1H), 2.94 (m, 1H), 3.40–3.50 (m, 1H), 4.15 (dd,1H), 4.36 (m,1H), 6.80 (d,1H), 6.48–6.55 (m,1H), 6.65–6.72 (m,1H), 7.00–7.18 (m,3H), 8.02–8.35 (br,1H)

[α]D (24° C., MeOH, c= 2.68)= –21.0°

Reference Example 1

1.75 g of the R(–)-5-(2,3-epoxypropoxy)quinoline obtained in Example 2 was suspended in 11 ml of isopropanol. The suspension was added to 10 ml of an isopropanol solution containing 3.1 g of dibenzosuberanylpiperazine. The mixture was stirred with heating, to obtain a complete solution. The solution was allowed to stand overnight at room temperature. The reaction mixture was concentrated. The residue was purified by silica gel column chromatography (chloroform:methanol= 50:1), followed by recrystallization from an ether-hexane mixed solvent, to obtain 3.08 g of intended R(+)-5-[3-{4-(dibenzosuberan-5-yl)piperazin-1-yl}-2-hydroxypropoxy] quinoline as colorless needle-like crystals.

Optical purity: 98.5% e.e.

Melting point: 112.5°–114° C.

Optical rotation [α]D=+20.8°

Reference Example 2

S(+)-5-(2,3-epoxypropoxy)quinoline was obtained in the same manner as in Example 2 with the exception that R(–)-glycidyl tosylate was replaced by S(+)-glycidyl tosylate. Using 1.92 g of the S(+)-5-(2,3-epoxypropoxy)quinoline, a reaction was conducted in the same manner as in Reference Example 1 to obtain 3.3 g of S(–)-5-[3-{4-(dibenzosuberan-5 -yl)piperazin-1-yl}-2-hydroxypropoxy] quinoline as colorless needle-like crystals.

Optical purity: 98.4% e.e.

Melting point: 112.5°–114° C.

Optical rotation [α]D= –21.4°

Reference Example 3

2.7 g of the R(−)-5-(2,3-epoxypropoxy)quinoline obtained in Example 2 was suspended in 20 ml of isopropanol. To the suspension was added 42 ml of an isopropanol solution containing 4.8 g of diphenylacetylpiperazine. The reaction mixture was stirred with heating, to obtain a complete solution. The solution was allowed to stand overnight at room temperature. The reaction mixture was concentrated. The residue was purified by silica gel column chromatography (chloroform:methanol= 40:1), followed by recrystallization from ethyl acetate to obtain 4.25 g of R(+)-5-[3-{4-(2,2-diphenylacetyl)piperazin-1 -yl}-2-hydroxypropoxy]quinoline as colorless needle-like crystals.

Optical purity: 96.9% e.e.
Melting point: 137°–140° C.
Optical rotation [α]D= +14.2°

Reference Example 4

S(+)-5-(2,3-epoxypropoxy)quinoline was obtained in the same manner as in Example 2 with the exception that R(−)-glycidyl tosylate was replaced by S(+)-glycidyl tosylate. Using 1.3 g of the S(+)-5-(2,3-epoxypropoxy)quinoline, a reaction was conducted in the same manner as in Reference Example 3 to obtain 2.1 g of S(−)-5-[3-{4-(2,2-diphenylacetyl)piperazin-1 -}-2-hydroxypropoxy]quinoline as colorless needle-like crystals.

Optical purity: 96.5% e.e.
Melting point: 137°–140° C.
Optical rotation [α]D= −14.8°

Fields of Industrial Application

The glycide derivative obtained in the present invention is an very important compound used as an intermediate in production of the carcinostaticity-enhancing agent of low toxicity and side effects, previously reported by the present inventors in Japanese Patent Application Kokai (Laid-Open) No. 101662/1991.

Also in production of a carcinostaticity-enhancing agent which is an optically active compound, the present invention enables production of an intended optically active compound at a good chemical yield at a good optical purity.

Thus, the present invention can be used for production of a carcinostaticity-enhancing agent expected to be useful in cancer chemotherapy.

We claim:
1. A process for producing a glycide derivative represented by the following general formula (I), which is characterized by reacting a hydroxyaryl or heteroaryl represented by A-OH with glycidyl tosylate in a solvent in the presence of a cesium base selected from the group consisting of cesium carbonate and cesium hydroxide:

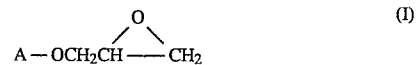

wherein A represent an aryl group or a heteroaryl group.

2. A process according to claim 1, wherein optically active glycidyl tosylate is used as the glycidyl tosylate and an optically active glycide derivative represented by the general formula (I) is produced.

3. A process according to claim 1 or 2, wherein the cesium base is cesium carbonate.

4. A process according to claim 3, wherein the A-OH is 5-hydroxyquinoline.

5. The process of claim 1, wherein said solvent is water, an organic solvent, or a mixture thereof.

6. The process of claim 5, wherein said organic solvent is an alcohol, an ether, an amide, a hydrocarbon, acetonitrile or dimethyl sulfoxide.

7. The process of claim 6, wherein said organic solvent is dimethylformamide.

8. The process of claim 1, wherein said reacting is conducted at from 0° to the boiling point of said solvent.

9. The process of claim 8, wherein said reacting is conducted at from room temperature to 70° C.

10. The process of claim 1, wherein 0.1 to 10 equivalents of cesium base are used per mole of A-OH.

11. The process of claim 10, wherein 1–3 equivalents of cesium base are used per mole of A-OH.

12. The process of claim 1, wherein an equimolar ratio of hydroxyaryl or heteroaryl and glycidal tosylate are used.

13. The process of claim 1, wherein said aryl group is phenyl, naphthyl or indenyl.

14. The process of claim 1, wherein said heteroaryl group is indolyl, furyl, thienyl, pyridyl, quinolyl, isoquinolyl, benzofuryl or thiadiazolyl.

15. The process of claim 1, wherein said glycidyl tosylate is glycidyl benzenesulfonate or glycidyl nitrobenzene-sulfonate.

* * * * *